US011702386B2

(12) United States Patent
Back et al.

(10) Patent No.: US 11,702,386 B2
(45) Date of Patent: Jul. 18, 2023

(54) PROCESSES FOR THE MANUFACTURE OF SECONDARY FATTY ALCOHOLS, INTERNAL OLEFINS AND INTERNAL OLEFIN SULFONATES

(71) Applicants: RHODIA OPERATIONS, Aubervilliers (FR); SOLVAY SA, Brussels (BE)

(72) Inventors: Olivier Back, Lyons (FR); Rémy Leroy, Mions (FR); Philippe Marion, Vernaison (FR)

(73) Assignees: Solvay SA, Brussels (BE); RHODIA OPERATIONS, Lyons (FR)

( * ) Notice: Subject to any disclaimer, the term of this patent is extended or adjusted under 35 U.S.C. 154(b) by 151 days.

(21) Appl. No.: 16/970,987

(22) PCT Filed: Feb. 21, 2018

(86) PCT No.: PCT/EP2018/054317
§ 371 (c)(1),
(2) Date: Aug. 19, 2020

(87) PCT Pub. No.: WO2019/161896
PCT Pub. Date: Aug. 29, 2019

(65) Prior Publication Data
US 2020/0399209 A1 Dec. 24, 2020

(51) Int. Cl.
*C07C 303/06* (2006.01)
*C07C 29/149* (2006.01)
*C07C 31/02* (2006.01)
*C07C 309/20* (2006.01)
*B01J 19/00* (2006.01)
*B01J 23/745* (2006.01)
*B01J 35/02* (2006.01)

(52) U.S. Cl.
CPC ......... *C07C 303/06* (2013.01); *B01J 19/0013* (2013.01); *B01J 23/745* (2013.01); *B01J 35/026* (2013.01); *C07C 29/149* (2013.01); *B01J 2219/00029* (2013.01); *C07C 31/02* (2013.01); *C07C 309/20* (2013.01)

(58) Field of Classification Search
CPC .... C07C 303/32; C07C 303/06; C07C 29/145
USPC ........................................................ 562/121
See application file for complete search history.

(56) References Cited

U.S. PATENT DOCUMENTS

| 3,646,106 A | 2/1972 | Carr |
| 4,950,763 A | 8/1990 | Schommer |
| 9,193,650 B1 | 11/2015 | Hommeltoft |
| 9,193,653 B1 | 11/2015 | Hommeltoft |
| 10,035,746 B2 | 7/2018 | Back et al. |
| 2014/0335586 A1 | 11/2014 | Zhang |
| 2014/0353250 A1 | 12/2014 | Semple et al. |
| 2017/0247603 A1 | 8/2017 | Perez-Regalado |

FOREIGN PATENT DOCUMENTS

| DE | 295657 C | 12/1916 |
| EP | 2468708 A | 6/2012 |
| WO | 2016177842 A1 | 11/2016 |

OTHER PUBLICATIONS

Machine Translation of DE295657.
Changxin Shi, Guangzhi Liao, Weidong Liu—Synthesis of Internal Olefin Sulfonate and its Application in Oil Recovery—Arabian Journal for Science and Engineering (2014) 39(1), pp. 37-41.
Albert L Henne, Alfred H Matuszak—The Dehydration of Secondary and Tertiary Alcohols—J. Am. Chem. Soc. (1944) 66(10), pp. 1649-1652—doi: 10.1021/ja01238a012.
Lukas J. Gooen, Patrizia Mamone, Christoph Oppel—Catalytic Decarboxylative Cross-Ketonisation of Aryl- and Alkylcarboxylic Acids using Magnetite Nanoparticles—Adv. Synth. Catal. (2011) 353, 57-63—DOI:10.1002/adsc.201000429.
R. Klimkiewicz, H. Grabowska, L. Syper—Oil Industry Waste as a Basis for Synthesis of New Type Surfactants—Polish Journal of Environmental Studies vol. 10, No. 5 (2001), 337-339.
Curtis, R. G.; Dobson, A. G.; Hatt, H. H.—The ketonization of higher fatty acids with some observations on the mechanism of the reaction. Pt. 6. Studies of waxes—Journal of the Society of Chemical Industry (1947) 66, 402-407—doi: 10.1002/jctb.5000661108.

*Primary Examiner* — Ana Z Muresan
(74) *Attorney, Agent, or Firm* — Osha Bergman Watanabe & Burton LLP

(57) ABSTRACT

Process $P^1$ for the manufacture of a secondary fatty alcohol, said process $P^1$ comprising synthesizing an internal ketone K1 by a process $P^0$ comprising the decarboxylative ketonization reaction of a fatty acid or the like in a liquid phase with a metal compound as catalyst in a reaction medium, wherein a ketone $K^2$ at liquid state, which is identical or similar to the internal ketone $K^1$, is introduced into the reaction medium, and subjecting the internal ketone $K^1$ to a hydrogenation reaction with hydrogen gas as hydrogenating agent to form the secondary fatty alcohol. Use of the secondary fatty alcohol manufactured by the process $P^1$ for the manufacture of an internal olefin or of an internal olefin sulfonate.

21 Claims, No Drawings

PROCESSES FOR THE MANUFACTURE OF SECONDARY FATTY ALCOHOLS, INTERNAL OLEFINS AND INTERNAL OLEFIN SULFONATES

This application is a U.S. national phase entry under 35 U.S.C. § 374 of International Application No. PCT/EP2018/054317, filed on Feb. 21, 2018, the entire content of which is explicitly incorporated herein by this reference.

The present invention relates to processes for the manufacture of secondary fatty alcohols, internal olefins and internal olefin sulfonates.

Chemical flooding technology is one of the promising technologies used in enhanced oil recovery (EOR). It often involves injection of a surfactant or surfactant formulation that will effectively displace remaining oil. However, conventional surfactants such as alkoxylated sulfates and petroleum sulfonates have several drawbacks, including poor thermal stability, low salt tolerance, and poor calcium or magnesium ions resistance. These drawbacks were overcome by internal olefin sulfonates (IOS) which can be used in high temperature, high salinity reservoirs and show excellent performance in case of high viscosity or high-wax crude oils. Besides, IOS show excellent performance in oil recovery when used as oil displacement agents in an ASP (alkaline-surfactant-polymer) flooding system.

IOS are generally prepared by sulfonation of internal olefins followed by alkaline hydrolysis. Internal olefins can be made through isomerization of alpha-olefins which can be obtained through oligomerization of ethylene following stoechiometric or catalytic Ziegler process or using Ni-based homogeneous catalyst such as in Shell Higher Olefin Process. Another way to obtain long chain internal olefins is by the initial conversion of fatty acids into respective internal ketones through decarboxylative ketonization; this transformation can be achieved by well-known processes which are commercially used. The so-obtained internal ketones can then be derivatized by subsequent reactions: firstly, a hydrogenation will transform the internal ketones to secondary fatty alcohols, which can then be dehydrated to obtain the internal olefins. All those transformations are well known in the art and some of them are commercially used.

Beyond their possible use as reaction intermediates in the manufacture of IOS, internal olefins can be used as synthetic drilling fluid base for high value, primarily off-shore synthetic drilling fluids. The higher internal olefins appear to form a more lubricious layer at the metal surface and are recognized as better lubricants. Another significant application for internal olefins is in paper sizing. Internal olefins can also serve as intermediates for the preparation of compounds other than IOS. For example, internal olefins can be reacted with maleic anhydride to make an alkyl succinic anhydride, a popular paper sizing chemical.

Beyond their possible use as reaction intermediates in the manufacture of IOS, secondary fatty alcohols can be used in various applications such as solvents, preservatives, etc. They can also serve as intermediates for the preparation of compounds other than IOS. As a first example, non-ionic surfactants can be obtained by alkoxylating the secondary fatty alcohols. As another example, secondary fatty alcohols can be engaged in a carbonylation reaction to obtain branched fatty acids.

In the sequence of reactions to obtain secondary fatty alcohols, internal olefins or IOS from fatty acids or fatty acid derivatives, the most delicate, perfectible part lies certainly in the conversion of these fatty acids or fatty acid derivatives into internal ketone intermediates.

The preparation of internal ketone from fatty acids can be carried out in the gas phase at temperatures usually exceeding 350° C. and usually above 400° C. for fatty acids in the presence of catalytic amounts of metal oxide compounds (e.g. $MgO$, $ZrO_2$, $Al_2O_3$, $CeO_2$, $MnO_2$, $TiO_2$).

Carrying out the reaction in the gas phase with fatty acids with a high boiling point is difficult as the evaporation of the reactants needs very high temperatures which are detrimental for the selectivity of the process and leads to the formation of undesired by-products.

In US 2014/335586 A, the reaction is carried out with medium-chain fatty acids. Thus, a feed of fatty acids having from 4 to 9 carbon atoms is mixed with some recycled ketone product having from 7 to 17 carbon atoms, and preheated to 300-400° C. before being fed to a fixed bed reactor packed with a metal oxide catalyst, typically with 20 percent $MnO_2$ or $CeO_2$ on alumina support. The reactor outflow is cooled down before being sent to a three phase separator. The vapor phase (comprising mostly $CO_2$) is vented, while the water phase may be removed from the bottom.

Carrying out the reaction in the liquid phase offers certain advantages over the reaction in the gas phase, e.g. usually higher productivities, better selectivity which is important for the subsequent work-up of the reaction mixture and finally allows getting reduced manufacturing costs.

In prior art liquid phase reaction processes, metals are usually employed in stoichiometric amounts to carry out the reaction. The reaction goes through the formation of metallic carboxylate salts which decompose to ketone and $CO_2$.

German patent DE 295 657 relates to a process for the manufacture of ketones where monocarboxylic acids having a boiling point exceeding 300° C. are heated in the liquid phase with small amounts of catalytically active metal compounds, silica gels or silicates to temperatures not substantially exceeding 300° C. The organic acid is mixed with the catalytically active species and subsequently heated to the desired reaction temperature. The process is reported to yield the desired ketones in good yield and purity. However, if the fatty acid starting material comprises fatty acids or fatty acid derivatives having a boiling point of less than 300° C. (which is the case for linear fatty acids having 12 carbon atoms or less such as lauric acid, capric acid, caprylic acid . . . ) in a more than insignificant amount, the process described in DE 295 657 does not lead to the desired ketones in good yields.

In EP2468708 document, cross-ketonization reactions are performed in non-aqueous solvent using magnetite nanopowders as catalyst to obtain arylalkylketone. However distillation under reduced pressure is required to separate the desired product from the high boiling solvent which can be costly at industrial scale. Furthermore, long reaction times (in their examples 21 h) are required to reach high yields.

There remains a need for improved processes for the manufacture of secondary fatty alcohols, internal olefins and internal olefin sulfonates using fatty acids and/or fatty acid derivatives as starting materials. Especially, there remains a need from improving the first part of these processes wherein internal ketones are prepared by decarboxylative ketonization of the fatty acids and/or fatty acid derivatives. There remains a need in this first part for forming the desired internal ketones in high yield, with only minor amounts (if at all) of undesired by-products which can be easily separated from the reaction mixture; in addition, costly unitary operations for isolating the internal ketones from e.g. high boiling point solvents, such as distillation under reduced pressure, should desirably be avoided.

These needs and still other ones are advantageously met by the processes for the manufacture of fatty secondary alcohols, internal olefins and internal olefin sulfonates in accordance with the present invention.

SUMMARY OF THE PRESENT INVENTION

The present invention concerns a process $P^1$ for the manufacture of a secondary fatty alcohol, said process $P^1$ comprising:
   synthesizing an internal ketone $K^1$ by a process $P^0$ comprising the decarboxylative ketonization reaction of a fatty acid, a fatty acid derivative or a mixture thereof in a liquid phase with a metal compound as catalyst in a reaction medium, wherein a ketone $K^2$ at liquid state, which is identical or similar to the internal ketone $K^1$, is introduced into the reaction medium, and
   subjecting the internal ketone $K^1$ to a hydrogenation reaction with hydrogen gas as hydrogenating agent to form the secondary fatty alcohol.

The present invention concerns also a process $P^2$ for the manufacture of an internal olefin, said process $P^2$ comprising:
   manufacturing a secondary fatty alcohol by the process $P^1$ as above described, and
   converting the secondary fatty alcohol into an internal olefin by a dehydration reaction.

Finally, the present invention concerns a process $P^3$ for the manufacture of an internal olefin sulfonate, said process $P^3$ comprising:
   manufacturing an internal olefin by the process $P^2$ as above described,
   sulfonating the internal olefin to form a sultone, and
   subjecting the sultone to an alkaline hydrolysis, so as to form the internal olefin sulfonate.

Process $P^0$ for Making Internal Ketones $K^1$
Summary of the Process $P^0$

An internal ketone $K^1$ is synthesized by a process $P^0$ comprising the decarboxylative ketonization reaction of a fatty acid, a fatty acid derivative or a mixture thereof in a liquid phase with a metal compound as catalyst in a reaction medium.

In accordance with process $P^0$, a ketone $K^2$ at liquid state, which is identical or similar to the internal ketone $K^1$, is introduced into the reaction medium.

In an embodiment, the ketone $K^2$ which is introduced in the reaction medium is identical to the internal ketone $K^1$ and, likewise $K^1$, has been synthesized (at an earlier point in time) in accordance with a previous process $P^0$.

The reaction medium can be substantially free of third solvents.

The metal compound is advantageously selected from iron oxides, such as FeO, $Fe_3O_4$ or $Fe_2O_3$.

Water formed during the reaction can be continuously removed from the reaction medium.

The fatty acid, fatty acid derivative or mixture thereof comprises advantageously at least 10 mol %, based on the entire amount of fatty acid and fatty acid derivative, of fatty acid having 12 carbon atoms or less or derivative of fatty acid having 12 carbon atoms or less or mixture thereof. According to an embodiment, one and only one fatty acid, such as capric acid or lauric acid, is used as starting material. According to another embodiment of the invention, a fatty acid cut is used as starting material.

The molar ratio of fatty acid, fatty acid derivative or mixture thereof to metal is in advantageously the range of from 6:1 to 99:1.

The reaction medium is advantageously maintained at a temperature ranging from 270° C. to 400° C., preferably until full conversion of the fatty acid or fatty acid derivative or mixture thereof and disappearance of optionally formed intermediate metallic salts.

According to an embodiment, the process $P^0$ comprises the steps of:
   a) introducing in any order at least part of the ketone $K^2$ at liquid state, at least part of the metal compound, at least part of the fatty acid, fatty acid derivative or mixture thereof into a reactor in order to synthesize the internal ketone $K^1$, said reactor optionally containing before said introduction, a part of the metal compound, and/or a part of the fatty acid, fatty acid derivative or mixture thereof and/or a part of the ketone $K^2$ and/or a part of the internal ketone $K^1$,
   b) recovering the internal ketone $K^1$ optionally together with the ketone $K^2$, and preferably together with the ketone $K^2$,
   c) optionally recycling at least part of the internal ketone $K^1$ and/or ketone $K^2$ and/or at least part of the metal compound to step a).

Preferably, step a) of process $P^0$ comprises the steps:
   a1) introducing at least part of the ketone $K^2$ at liquid state, and at least part of the metal compound into a reactor, said reactor optionally containing before said introduction, a part of the metal compound, and/or a part of the fatty acid, fatty acid derivative or mixture thereof, and/or a part of the ketone $K^2$ and/or a part of the internal ketone $K^1$,
   a2) introducing at least part of the fatty acid, fatty acid derivative or mixture thereof into the reactor, optionally with:
      a part of the metal compound, and/or
      a part of the ketone $K^2$ and/or,
      a part of the intermediate metallic carboxylate salts obtained by reacting metal compound and the fatty acid or fatty acid derivative or mixture thereof before decomposition to form the internal ketone $K^1$.

Preferably, at step a) of process $P^0$, the fatty acid, fatty acid derivative or mixture thereof is introduced sequentially or continuously into the reactor.

According to an embodiment, during step a1), the reactor is substantially free of fatty acid and fatty acid derivative.

The process $P^0$ is easy to implement since it is performed in a liquid phase, and generally at ambient pressure.

The process $P^0$ uses substoechiometric (catalytic) amount of metal compound and does not need the further use of a third solvent; the isolation of product ketones from reaction mixture is therefore easier.

The process $P^0$ provides internal ketones with a high yield and selectivity with a relatively short reaction time and high productivity.

Detailed Description of the Process $P^0$

According to process $P^0$, a ketone $K^1$ is synthesized by decarboxylative ketonization reaction of a fatty acid, a fatty acid derivative or a mixture thereof in a liquid phase with a metal compound as catalyst in a reaction medium. An original technical feature of process $P^0$ is that a ketone $K^2$ at liquid state, which is identical or similar to the internal ketone $K^1$, is introduced into the reaction medium.

Suitable metals for use in the process $P^0$ in accordance with the present invention are selected from the group consisting of Mg, Ca, Al, Ga, In, Ge, Sn, Pb, As, Sb, Bi, Cd and transition metals having an atomic number of from 21 to 30. Suitable metal compounds are oxides of the aforementioned metals, carboxylate salts of the aforementioned metals, naphthenate salts of the aforementioned metals or acetate salts of the aforementioned metals, preferably metal compounds are oxides of the aforementioned metals. Magnesium, iron, and their oxides, are particularly preferred as metal compounds.

In accordance with a preferred embodiment the metal compound is iron(II) oxide or iron(III) oxide or a mixed oxide of iron(II) and iron (III) such as e.g. FeO, $Fe_3O_4$ or $Fe_2O_3$. Iron powder has economical advantages as it is cheap and abundantly available. It has been observed that iron oxides are efficient to promote the reaction reducing the overall reaction times.

According to the invention, the catalysis of the reaction may be qualified as a homogeneous catalysis since in the reaction conditions an intermediate metal carboxylate salt (i.e. iron carboxylate) is formed through the initial reaction between the fatty acid or its derivative with the metal compound and this intermediate salt is substantially soluble in the reaction medium.

The process $P^0$ of the invention can be a continuous or a batch process.

The process $P^0$ can be conducted at various scales. When the process $P^0$ is a batch process, at least 1 g, at least 1 kg, at least 10 kg, at least 100 kg or even at least 1 ton of internal ketone $K^1$ can be synthesized by batch. When process $P^0$ is a continuous process, the internal ketone $K^1$ can be synthesized at a pace of at least 1 g/h, at least 1 kg/h, at least 10 kg/h, at least 100 kg/h or even at least 1 ton/h.

As above indicated, in process $P^0$, a ketone $K^2$ at liquid state is introduced into the reaction medium.

The ketone $K^2$ can be identical or similar to the internal ketone $K^1$ to be synthetized.

The ketone $K^2$ has usually a boiling point of at least 170° C., advantageously of at least 220° C., preferably of at least 270° C., more preferably of at least 290° C. and even more preferably of at least 310° C. On the other hand, the boiling point of the ketone $K^2$ is usually of at most 600° C., preferably of at most 500° C. and more preferably of at most 410° C. As herein used, the term "boiling point" generally denotes the normal boiling point (also called the atmospheric boiling point or the atmospheric pressure boiling point) of a liquid; it corresponds to the case in which the vapor pressure of the liquid equals the defined atmospheric pressure at sea level, 1 atmosphere. It can be measured by differential scanning calorimetry using for example a METTLER Toledo equipment.

By "a ketone $K^2$ similar to the internal ketone $K^1$", it is meant that the difference between the boiling point of the internal ketone $K^1$ and the boiling point of the ketone $K^2$ is equal to or lower than 80° C. Preferably, the difference between the boiling point of the internal ketone $K^1$ and the boiling point of the ketone $K^2$ is equal to or lower than 40° C., preferably equal to or lower than 10° C., more preferably equal to or lower than 5° C., even more preferably equal to or lower than 3° C.

Non limitative examples of ketones suitable as ketone $K^2$ in accordance with the present invention are 5-nonanone (bp: about 186-187° C.), methyl levulinate (bp: about 193-195° C.), acetophenone (bp: about 202° C.), propiophenone (bp: about 218° C.), 6-undecanone (bp: about 228° C.), 7-tridecanone (bp: about 261° C.), 8-pentadecanone (bp: about 291° C.), benzophenone (bp: about 305° C.), 8-heptadecanone (predicted bp: about 309° C.), 8-octadecanone (predicted bp: about 323° C.), benzoin (bp: about 339-343° C.), 10-nonadecanone (predicted bp: about 343° C.), anthraquinone (bp: about 379-381° C.), 12-tricosanone (predicted by: about 387° C.), trans, trans dibenzylideneacetone (bp: about 401° C.), 13-pentacosanone (predicted by: about 410° C.), 14-heptacosanone (predicted bp: about 432° C.), 16-hentriacontanone (predicted bp: about 472° C.), 18-pentatriacontanone (bp: about 490° C.), 19-heptatriacontanone (predicted bp: about 523° C.) and 20-nonatriacontanone (predicted bp: about 532° C.).

The ketone $K^2$ is preferably an internal ketone. The ketone $K^2$ is more preferably one or more ketone(s) selected from internal ketones $K^1$ synthesized or susceptible of being synthesized by the process $P^0$.

Besides, the ketone $K^2$ is or includes one or more ketone(s) selected from ketones having preferably from 7 to 47 carbon atoms, more preferably from 15 to 43 carbon atoms, still more preferably from 19 to 39 carbon atoms and even more preferably from 23 to 35 carbon atoms.

Finally, the ketone $K^2$ is advantageously one or more ketone(s) selected from aliphatic ketones.

The ketone $K^2$ can consist of one and only one ketone or may be a mixture of ketones.

Possibly, the ketone $K^2$ is obtained or is susceptible of being obtained by decarboxylative ketonization reaction of a fatty acid, a fatty acid derivative or a mixture thereof.

When ketone $K^2$ is a mixture of ketones, said mixture may be homogeneous (i.e. uniform in composition) or heterogeneous; it is preferably homogeneous. When ketone $K^2$ is a mixture of ketones, the ketones of which the mixture is composed are generally at least partially miscible with each other; they are preferably fully miscible with each other. When ketone $K^2$ is a mixture of ketones, said mixture of ketones has advantageously one and only one boiling point. In case of a mixture of ketones, the expression "boiling point of the ketone" is to be understood as the boiling point of the mixture of ketones when said mixture of ketones has one and only one boiling point and as the lowest boiling point of the mixture of ketones when said mixture of ketones has several boiling points.

According to an embodiment, the ketone $K^2$ introduced into the reaction medium (in particular, the ketone $K^2$ introduced into the reactor at step a) of process $P^0$) has been synthesized in accordance with a previous process $P^0$, that is to say in accordance with a process $P^0$ that has been operated at an earlier point in time. Otherwise said, part of the ketone $K^1$ constituting the product synthesized by a previous process $P^0$ can be subsequently used/recycled as ketone K2 of present process $P^0$.

Previous process $P^0$ is preferably identical to the process $P^0$ of the present invention, that is to say that previous process $P^0$ and present process $P^0$ are preferably operated using the same recipes (including the nature and amounts of the reactants and the operating conditions).

So, when process $P^0$ is a batch process, the ketone $K^2$ introduced into the reaction medium of a current batch has advantageously been synthesized as internal ketone $K^1$ during a previous batch. The case being, the same fatty acid, fatty acid derivative or mixture thereof is preferably used as starting material for both batches and more preferably the whole recipes of both batches (including the nature and amount of all the ingredients involved in process $P^0$ and the operating conditions of process $P^0$) are identical to each other.

When process $P^0$ is a continuous process with a continuous reactor having an entry and an exit (e.g. a tubular reactor), part of the internal ketone $K^1$ which exits the continuous reactor is advantageously isolated from the reaction medium and recycled as ketone $K^2$, i.e. it is re-introduced as solvent into the reaction medium at the entry or close to the entry of the continuous reactor, where no or little ketone K1 has usually been synthesized yet.

The skilled person will easily understand that, when process $P^0$ is operated iteratively with use/recycling of internal ketone product $K^1$ as ketone solvent $K^2$, initialization (i.e. the very first batch in case of a batch process and the very first time in case of a continuous process) must be conducted by introducing in the reaction medium a ketone $K^2$ which is available otherwise than by being synthesized by process $P^0$ itself. Many ketones $K^2$ are commercially available products and/or can be prepared by any known other processes, notably by any one of the above described prior art processes or by the special prior art process described in WO 2016177842 (the whole content of which being herein incorporated by reference for all purposes) which can be operated in the absence of added solvent. When the fatty acid(s)/fatty acid derivatives(s) used for synthesizing the ketone $K^2$ is identical to the fatty acid(s)/fatty acid(s) derivative(s) used for synthesizing the internal ketone $K^1$ of the process $P^0$ of the invention, the ketone $K^2$ is generally similar or identical to the internal ketone $K^1$.

As herein used, the terms "fatty acid" refer to a carboxylic acid containing at least 4 carbon atoms. Besides, a fatty acid contains generally at most 28 carbon atoms. The terms "fatty acid derivative" refer to an anhydride made by the condensation of 2 fatty acids or to an ester made by the condensation of a fatty acid with an alcohol.

Suitable fatty acid derivatives are esters and anhydrides of fatty acids, but the use of free fatty acids as such is generally preferred. The esters or anhydrides in the course of the reaction are converted to the acids which then react with the metal or the metal compound. Especially in case of esters, however, alcohols are formed as a by-product which then has to be removed at a later point in time, which requires additional step and costs. However, if esters are derived from lower alcohols such as for example methanol, ethanol, propanol or butanol, the alcohols may be removed progressively over the course of the reaction thanks to a reactive distillation.

The fatty acids or fatty acid derivatives can be used in the form of so called fatty acids or fatty acid derivatives cuts, i.e. mixtures of fatty acids or fatty acid derivatives which can be obtained by the hydrolysis or alcoholysis of different natural fats and oils. Accordingly, these cuts may contain various amounts of different linear fatty acids or linear fatty acid derivatives with different chain lengths. Just by way of examples, fatty acid cuts obtained from coconut oil and comprising mainly $C_{12}$-$C_{18}$ fatty acids can be mentioned here. The skilled person is well aware of other fatty acid cuts obtainable form various sources and will select the best suitable starting materials based on the desired ketones.

According to an embodiment of the invention, fatty acids having 12 carbon atoms or less, preferably of from 8 to 12 carbon atoms or derivatives of such acids (esters or anhydrides) constitute at least 10 mol % and preferably at least 15 mol % of the entire molar amount of a fatty acid mixture or fatty acid derivative mixture used as starting material. These acids lead to ketones having a total carbon number of 23 or less which have proved to be advantageous in certain applications. In this embodiment, there is no specific upper limit for the amount of these fatty acids or fatty acid derivatives of acids having 12 carbon atoms or less, i.e. the starting material may entirely consist of such fatty acids and/or such fatty acid derivatives.

Fatty acids for use in the process $P^0$ of the present invention have generally at least 6 carbon atoms, such as hexanoic acid, caprylic acid, capric acid, lauric acid, myristic acid, palmitic acid, stearic acid, isostearic acid, arachidic acid, behenic acid, lignoceric acid, cerotic acid and mixtures thereof, and preferred fatty acid derivatives are the esters and anhydrides of these acids. The fatty acids have preferably at least 8 carbon atoms, more preferably at least 10 carbon atoms, still more preferably at least 12 carbon atoms; besides, they have preferably at most 24 carbon atoms, more preferably at most 22 carbon atoms, still more preferably at most 20 carbon atoms and the most preferably at most 18 carbon atoms.

The fatty acids may be free of any —C═C— double bond of and of any —C≡C— triple bond. Non limitative examples of such fatty acids are the previously cited caprylic acid, capric acid, lauric acid, myristic acid, palmitic acid, stearic acid and mixtures thereof.

Alternatively, the fatty acids may comprise one or more double bond(s) and/or one or more triple bond(s). Examples of fatty acids comprising one or more double bond(s) are oleic acid, linoleic acid, linolenic acid, erucic acid, palmitoleic acid, ricinoleic acid and mixtures thereof. Examples of fatty acids comprising one or more triple bond(s) are tariric acid, santalbic acid (which also comprises one double bond) and mixtures thereof.

In the fatty acids, the carbon atom which is adjacent to the carboxyl group can be secondary, tertiary or quaternary carbon atom. It is preferably a secondary or tertiary carbon atom. Very preferably, the carbon atom which is adjacent to the carboxyl group is a secondary carbon atom, that is to say that a methylene group is adjacent to the carboxyl group.

When starting from a single fatty acid, a single symmetrical ketone is obtained as the reaction product; when starting from a cut of fatty acids as described above all the ketones $K^1$ formed by the combination of the different alkyl groups of the starting acids are obtained and the distribution of the different mixed ketones $K^1$ generally follows a statistical binomial law. The reaction equation can be summarized as follows:

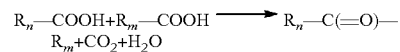

wherein $R_n$ and $R_m$ represent the aliphatic, e.g. alkyl, groups of the fatty acids present in the cut. It is well apparent that e.g. if three different acids are present, a total of six different ketones may be formed; three symmetrical ketones wherein $R_n$ and $R_m$ are identical and three mixed ketones with different groups $R_n$ and $R_m$.

The internal ketone $K^1$ synthesized by the process $P^0$ is generally a compound of formula (I)

wherein $R_n$ and $R_m$ independently represent an aliphatic group, generally a $C_3$-$C_{27}$ aliphatic group, very often a $C_3$-$C_{19}$ aliphatic group, often a aliphatic $C_7$-$C_{17}$ group. Internal ketones $K^1$ wherein $R_n$ and $R_m$ have from 10 to 20 carbons are preferred, and internal ketones $K^1$ wherein $R_n$ and $R_m$ have from 12 to 18 carbon atoms are much preferred.

The number of carbon atoms of $R_n$ and $R_m$ can be even or odd numbers. They are advantageously odd numbers, which happens typically when the internal ketone $K^1$ is made from a fatty acid containing an even number of carbon atoms (e.g. a $C_{23}$ internal ketone is made from a $C_{12}$ fatty acid).

For the reasons above explained when detailing the process $P^0$, $R_n$ and $R_m$ may be identical to each other; alternatively, $R_n$ and $R_m$ may differ from each other.

The number of carbon atoms of $R_n$ and of $R_m$, as herein represented by the couple (n,m), can be notably any of the following couples:

(3,3), (5,5), (7,7), (9,9), (11,11), (13,13), (15,15), (17,17), (19,19), (21,21), (23,23), (25,25), (27, 27)

(7,9), (7,11), (7,13), (7,15), (7,17), (7,19), (7,21), (7,23), (7,25), (7,27)

(9,11), (9,13), (9,15), (9,17), (9,19), (9,21), (9,23), (9,25), (9,27)

(11,13), (11,15), (11,17), (11,19), (11,21), (11,23), (11,25), (11,27)

(13,15), (13,17), (13,19), (13,21), (13,23), (13,25), (13,27)

(15,17), (15,19), (15,21), (15,23), (15,25), (15,27)

(17,19), (17,21), (17,23), (17,25), (17,27)

(19,21), (19,23), (19,25), (19,27)

(21,23), (21,25), (21,27)

(23,25), (23,27) or (25,27).

The aliphatic groups $R_n$ and $R_m$ may be linear or branched.

The aliphatic groups $R_n$ and $R_m$ may be free of any double bond and of any triple bond. Alternatively, the aliphatic groups $R_n$ and $R_m$ may comprise at least one —C═C— double bond and/or at least one —CH≡C— triple bond.

The aliphatic groups $R_n$ and $R_m$ are advantageously chosen from alkyl groups, alkenyl groups, alkanedienyl groups, alkanetrienyl groups and alkynyl groups.

Preferably, the aliphatic groups $R_n$ and $R_m$ are independently chosen from chosen from alkyl and alkenyl groups.

More preferably, the aliphatic groups $R_n$ and $R_m$ are independently chosen from alkyl and alkenyl groups, generally from $C_3$-$C_{27}$ alkyl and $C_3$-$C_{27}$ alkenyl groups, very often from $C_3$-$C_{19}$ alkyl and $C_3$-$C_{19}$ alkenyl groups and often from $C_6$-$C_{17}$ alkyl and $C_6$-$C_{17}$ alkenyl groups. More preferably, $R_n$ and $R_m$ independently represent an alkyl group, generally a $C_3$-$C_{27}$ alkyl group, very often a $C_3$-$C_{19}$ alkyl group, often a $C_6$-$C_{17}$ alkyl group.

In internal ketones $K^1$, each of the two carbon atoms which are adjacent to the carbonyl group can be secondary, tertiary or quaternary carbon atoms. Both are preferably secondary or tertiary carbon atoms. Very preferably, both carbon atoms which are adjacent to the carbonyl group are secondary carbon atoms, that is to say that methylene groups are adjacent to the carbonyl group; the case being, internal ketones $K^1$ of formula (I)

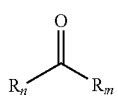

(I)

as above defined, can be represented by formula (II)

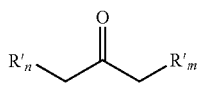

(II)

wherein $R'_n$ and $R'_m$ independently represent an aliphatic group, generally a $C_2$-$C_{26}$ aliphatic group, very often a $C_2$-$C_{18}$ group, often a $C_5$-$C_{16}$ group.

According to an embodiment, the total amount of fatty acid material (fatty acid plus fatty acid derivative) added in the reaction medium for the decarboxylative ketonization reaction is such that the overall molar ratio of metal to carboxylic groups is in the range of from 1:6 to 1:99, i.e. the amount of metal is about 1 mol % to about 14 mol % and preferably of from 2 to about 10 mol % of the entire amount of fatty acid and fatty acid derivative.

For most of the processes described in the prior art in the liquid phase the metal or metal compound was used in amounts of more than 50 mol % and in many cases even exceeding equimolar amounts. Such high amounts of metal are not necessary in the process $P^0$ in accordance with the present invention which is a technical as well as an economical advantage of the process $P^0$ in accordance with the present invention over the prior art.

During the decarboxylative ketonization reaction, the temperature of the reaction medium inside the reactor may be maintained at high temperature, for example the temperature inside the reactor may range from 270° C. to 400° C., preferably from 285° C. to 350° C., more preferably from 300 to 350° C. The reaction medium may be maintained at high temperature until full conversion of fatty acid and disappearance of the optionally formed intermediate metallic salts.

The process $P^0$ of the present invention is preferably carried out in an unpressurized system, i.e. without applying superatmospheric pressure. The by-products water and carbon dioxide can be continuously removed during the course of the reaction. Suitable equipment is known to the skilled person and he will use the best suitable equipment set-up for the specific situation. Only by way of example, a so called Dean-Stark trap can be used to remove the water formed during the reaction and such removal represents a preferred embodiment of the present invention.

During the process of the invention, a reaction medium comprising:

at least part of a ketone $K^2$, at least part of the metal compound, and at least part of the fatty acid, fatty acid derivative or mixture thereof, may be obtained.

According to a particular embodiment of the invention, the process comprises the steps of:

introducing at least part of the ketone $K^2$ at liquid state, at least part of the metal compound, at least part of the fatty acid, fatty acid derivative or mixture thereof into a reactor in order to synthesize the internal ketone $K^1$, said reactor optionally containing, before said introduction, a part of the metal compound, a part of the fatty acid, fatty acid derivative or mixture thereof, a part of the ketone $K^2$ and/or a part of the internal ketone $K^1$, recovering the internal ketone $K^1$ together with the ketone $K^2$, optionally recycling at least part of the internal ketone $K^1$ and ketone $K^2$ and/or at least part of the metal compound to step a).

The reaction medium may be formed in the reactor by introducing the different compounds at step a) according to any introduction policy.

According to a preferred embodiment, the metal compound is not mixed with the fatty acid or fatty acid derivative or mixture thereof before introduction into the reactor, in order to avoid the formation of metallic salt outside the reaction medium.

According to an embodiment of the invention, the process $P^0$ of the invention further comprises an additional step after step a) and before step b) of maintaining the temperature of the reactor at a high temperature, preferably at a temperature ranging from 270° C. to 400° C., more preferably from 285 to 350° C., even more preferably from 300 to 350° C., until full conversion of fatty acid and disappearance of the optionally formed intermediate metallic salts.

According to an embodiment, the step a) of the previous embodiment of the process $P^0$ of the invention comprises the steps of:

a1) introducing at least part of the ketone $K^2$ at liquid state, and at least part of the metal compound into a reactor, said reactor optionally containing, before said introduction, a part of the metal compound, a part of the fatty acid, fatty acid derivative or mixture thereof, a part of the ketone $K^2$ and/or a part of the internal ketone $K^1$, a2) introducing at least part of the fatty acid, fatty acid derivative or mixture thereof into said reactor, optionally with a part of the metal compound and/or a part of the ketone $K^2$ and/or a part of the intermediate metallic carboxylate salts obtained by reacting metal compound and fatty acid or fatty acid derivative or mixture thereof before decomposition to form the internal ketone $K^1$.

According to an embodiment of the invention, all the ketone $K^2$ may be introduced during step a1) and/or all the fatty acid or fatty acid derivative or mixture thereof may be introduced during step a2).

According to an embodiment wherein the fatty acid, fatty acid derivative or mixture thereof is mixed with the metal compound before introduction into the reaction medium, metallic carboxylate salts may be obtained by a reaction between metal compound and the fatty acid, fatty acid derivative or mixture thereof; said reaction can be carried out at a temperature lower than 270° C.

According to said embodiment, the ketone $K^2$ and the metal compound introduced at step a1) may be introduced separately or together into the reactor. Indeed, the ketone $K^2$ and the metal compound may be mixed outside the reactor, before their introduction into the reactor or the ketone $K^2$ and the metal compound may be mixed into the reactor after their separate introduction into the reactor.

During step a1), at least part of the metal compound is also introduced into the reactor. According to an embodiment, the reactor initially comprises, before step a1), a part of the metal compound, for example, after implementation of step b) (recovery of the synthetized ketones), a part of the metal compound remains in the reactor. According to another embodiment, all of the metal compound is introduced into the reactor during step a1).

According to an embodiment of the invention, at step a1), the reactor is substantially free, in particular totally free, of fatty acid and fatty acid derivative. According to said embodiment, when the ketone $K^2$ is introduced into the reactor, said reactor is substantially free of fatty acid and substantially free of fatty acid derivative.

During step a2), the fatty acid, fatty acid derivative or mixture thereof are introduced in the liquid state into the reactor containing the ketone $K^2$ and the metal compound, for example through a funnel equipping the reactor. They may be added sequentially or continuously and they are profitably added at a rate avoiding the build-up of substantial amounts of free acid in the reaction system as well as significant temperature drop. The progress of the reaction and the conversion of the starting materials to the ketones $K^1$ as final products may be conveniently monitored through appropriate methods like IR analysis.

During step a2), the fatty acid, fatty acid derivative or mixture thereof is generally added over a period of time which depends notably on the overall amount of acid or acid derivative used as well as the overall amount of metal compound present into the reactor.

Once the fatty acid derivative or fatty acid added in the process $P^0$ of the invention has been converted, the desired internal ketone $K^1$ can be recovered e.g. by distillation at reduced pressure. One can take also advantage of the ferromagnetic properties of the at least one metallic compound formed during the reaction (such as iron oxide(s)) to separate the metallic compound from the ketone by applying a magnetic field.

Another way to separate the ketone from the metal compound is through a simple decantation or a simple filtration as the metallic compound is not soluble in the reaction mixture containing the ketone obtained as the reaction product. The skilled person is aware of representative techniques so that no further details need to be given here.

At step b), the internal ketone $K^1$ and the ketone $K^2$ may be recovered together or separately, but preferably together. Indeed, according to a preferred embodiment of the invention, the ketone $K^2$ and the internal ketone $K^1$ are not separated.

The entire process $P^0$ is advantageously carried out under inert gas atmosphere and suitable inert gases are e.g. nitrogen or argon, to name only two examples.

The process $P^0$ can also be done in a continuous way where iron oxides are separated off from the reaction product in another/third separation zone and the residue constituted mainly of iron oxide can be recycled back into the reactor. It has been found, that up to four cycles are possible without a significant loss of catalytic activity of the metal or metal compound.

In another embodiment of the process $P^0$ of the present invention, at the end of step a) the metallic compounds are separated from the products, e.g. using conventional techniques, and then are recycled for the conversion of another batch of fatty acid or fatty acid derivative or mixture thereof preferably comprising at least 10 mol %, based on the entire amount of fatty acid and fatty acid derivative, of fatty acid having 12 carbon atoms or less or derivative of such fatty acid or mixture thereof.

In a same way, part of the ketones recovered at step b) can be recycled in order to perform step a) of the process $P^0$.

The yield of the desired ketones after step a) normally exceeds 60%, more preferably 70% and can be as high as more than 90%.

According to an embodiment of the process $P^0$ of the invention, the reaction medium in the reactor does not contain substantial amount of a third solvent. In a particularly preferred embodiment, no substantial amount of third solvent is added during the process $P^0$ of the invention.

For example, the reactor preferably comprises less than 5% by weight of third solvent(s), more preferably less than 3% by weight of third solvent(s), even more preferably less than 1% by weight of third solvent(s), based on the total weight of the reaction medium, ideally the reactor comprises no third solvent(s).

Within the meaning of the present invention, by the expression "third solvent", it is to be understood, a solvent different from the internal ketone $K^1$, the ketone $K^2$, the fatty acid or fatty acid derivative, the by-products that could be generated during the reaction.

Within the meaning of the present invention, the expression "reaction medium" refers to the medium, within the reactor, wherein the decarboxylative ketonization reaction takes place.

The reactor may be any kind of reactors that are conventionally used for the synthesis of ketones, in particular for the synthesis of ketones in liquid phase.

Within the meaning of the present invention, by "side reactions products", it is to be understood any product formed during the decarboxylative ketonization reaction different from ketones. Among side reaction products, mention may be made of hydrocarbons such as alkanes or alkenes.

Use of the Internal Ketones $K^1$ for the Manufacture of Secondary Fatty Alcohols—Process $P^1$ In accordance with the process $P^1$, the internal ketone $K^1$ synthesized from a fatty acid, a fatty acid derivative or a mixture thereof in accordance with the process $P^0$ is then used for the manufacture of the respective secondary fatty alcohol. To obtain the secondary fatty alcohol, the internal ketone $K^1$ is subjected to a hydrogenation reaction.

So, when the internal ketone $K^1$ is of formula (I), a secondary fatty alcohol of formula

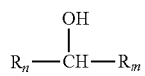

(III)

is usually formed, with $R_m$ and $R_n$ as previously defined for the internal ketone $K^1$ of formula (I).

In particular, when the internal ketone $K^1$ is of formula (II), a secondary fatty alcohol of formula

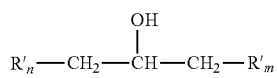

(IV)

is usually formed, with $R'_m$ and $R'_n$ as previously defined for the internal ketone $K^1$ of formula (II).

In accordance with process $P^1$, this hydrogenation reaction is achieved by reacting the internal ketone $K^1$ with hydrogen gas.

The reaction is usually carried out in the presence of a catalyst. The catalyst includes advantageously a transition metal, such as palladium. Besides, the catalyst is advantageously a supported catalyst. Preferably, the catalyst is a heterogeneous transition metal catalyst on a support, such as carbon. Just by way of example, palladium catalysts supported on carbon materials can be mentioned. Sponge catalysts like Raney metals can also be cited.

The hydrogenation reaction is usually carried out at a hydrogen pressure of from 500 kPa to 10000 kPa. The hydrogen pressure is preferably of at least 1000 kPa, more preferably of at least 2000 kPa; besides, the hydrogen pressure is preferably of at most 6000 kPa, more preferably of at most 4000 kPa.

The hydrogenation reaction is usually carried out at a temperature in the range of from 50° C. to 300° C. The reaction temperature is preferably of at least 100° C., more preferably of at least 120° C.; besides, the reaction temperature is preferably of at most 250° C., more preferably of at most 200° C.

The hydrogenation reaction is advantageously made without adding any solvent to the hydrogenation medium.

The hydrogenation reaction can be made in an autoclave equipped with a radial flow impeller.

The hydrogenation reaction can be made batchwise or continuously, as it is the case for process $P^0$. Hence, process $P^1$ as a whole can also be a batch or continuous process.

The fatty secondary alcohol that has been formed during the hydrogenation reaction can be recovered using conventional separation techniques, such as filtration and/or extraction by a solvent followed by evaporation of this solvent.

The hydrogenation reaction and, more generally, the whole process $P^1$ can be conducted at various scales.

When the hydrogenation reaction is made batchwise, at least 1 g, at least 1 kg, at least 10 kg, at least 100 kg or even at least 1 ton of secondary fatty alcohol can be formed by hydrogenation batch. When the hydrogenation reaction is made continuously, the secondary fatty alcohol can be formed at a pace of at least 1 g/h, at least 1 kg/h, at least 10 kg/h, at least 100 kg/h or even at least 1 ton/h.

When the whole process $P^1$ is made batchwise, at least 1 g, at least 1 kg, at least 10 kg, at least 100 kg or even at least 1 ton of secondary fatty alcohol can be manufactured by batch. When the whole process $P^1$ is made continuously, the secondary fatty alcohol can be manufactured at a pace of at least 1 g/h, at least 1 kg/h, at least 10 kg/h, at least 100 kg/h or even at least 1 ton/h.

Use of the Secondary Fatty Alcohols for the Manufacture of Internal Olefins—Process $P^2$ The secondary fatty alcohols manufactured by the process $P^1$ may be further converted into internal olefins.

With this regard, the present invention concerns a process $P^2$ for the manufacture of an internal olefin, said process $P^2$ comprising:

manufacturing a secondary fatty alcohol by the process $P^1$ as previously described, and converting the secondary fatty alcohol into an internal olefin by a dehydration reaction.

As well known to the skilled person, the dehydration reaction of a secondary alcohol results in the formation of a —C=C— double bond and in the elimination from the secondary alcohol of its hydroxyl group and of one hydrogen atom that was linked to one out of the two carbon atoms adjacent to the carbon atom bearing the hydroxyl group. Hence, in accordance with process $P^2$, at least one out of the two carbon atoms which are adjacent to the carbon atom bearing the hydroxyl group of the secondary fatty alcohol must be a secondary or tertiary carbon. This is this the case when, in the internal ketone $K^1$ manufactured by the process $P^0$, at least one out of the two carbon atoms which are adjacent to the carbonyl group of the internal ketone $K^1$ is a secondary or tertiary carbon, which itself happens when the process $P^0$ uses as starting material at least one fatty acid, fatty acid derivative or mixture thereof, wherein the carbon atom of the fatty acid which is adjacent to the carboxyl group is a secondary or tertiary carbon.

In accordance with process $P^2$, both carbon atoms which are adjacent to the carbon atom bearing the hydroxyl group of the secondary fatty alcohol are preferably secondary or tertiary carbons. Besides, in accordance with process $P^2$, at least one out of the two carbon atoms which are adjacent to the carbon atom bearing the hydroxyl group of the secondary fatty alcohol is preferably a secondary carbon. Very preferably, both carbon atoms which are adjacent to the carbon atom bearing the hydroxyl group of the secondary fatty alcohol are secondary carbons.

Suitable secondary fatty alcohols suitable for process $P^2$ include alcohols of formula

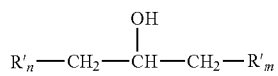
(IV)

with $R'_m$ and $R'_n$ as previously defined for internal ketone $K^1$ of formula (II).

Internal olefins formed by dehydration of the secondary fatty alcohol of formula (IV) are or include internal olefins of formula(e)

(V)

(V')

wherein (V) and (V') are identical to or different from each other.

Since the double bond is formed next to the alcohol group which is removed, the internal olefins have the double bond mainly in the middle of the chain when $R'_m=R'_n$ (which is the case when one and only fatty acid is used as starting material of process $P^0$).

Some limited isomerisation of the —C═C— bond may occur. However, the internal olefin manufactured by the process $P^2$ show generally a very low degree of isomerization of the double bond, if any.

It is thus apparent that the structure of the internal olefin obtained by the process $P^2$ is mainly or essentially determined by the structure of the starting secondary fatty alcohol, which in turn is essentially determined by the structure of the starting internal ketone, which in turn is essentially determined by the structure of the starting fatty acid.

The dehydration reaction is advantageously carried out in an inert atmosphere, for example in an argon atmosphere.

The dehydration is advantageously carried out in the substantial absence of added solvent, preferably in the absence of added solvent.

The dehydration reaction is generally made in the presence of a catalyst, such as a metal oxide catalyst. Aluminum oxide is preferred, and $\eta\text{-}Al_2O_3$ is much preferred.

Water generated by the dehydration reaction is advantageously progressively eliminated during the course of this reaction.

The dehydration reaction is advantageously made at a temperature in the range of from 150° C. to 450° C. The dehydration reaction temperature is preferably of at least 200° C. and more preferably of at least 250° C.; besides, it is preferably of at most 400° C. and more preferably of at most 350° C.

The duration of the dehydration reaction ranges generally from about 30 min to about 6 h.

Use of the Internal Olefins for the Manufacture of Internal Olefin Sulfonates (IOS)—Process $P^3$ The internal olefins manufactured by the process $P^2$ may be further converted into internal olefin sulfonates.

With this regard, the present invention concerns a process $P^3$ for the manufacture of an internal olefin sulfonate, said process $P^3$ comprising:
  manufacturing an internal olefin by the process $P^2$ as previously described,
  sulfonating the internal olefin to form a sultone, and
  subjecting the sultone to an alkaline hydrolysis, so as to form the internal olefin sulfonate.

"Internal olefin sulfonate" (IOS) as used herein means at least one sulfonate compound that can be obtained by the above process $P^3$.

The IOS consists generally of at least one monosulfonate or of at least one monosulfonate and at least one polysulfonate.

As herein used, a polysulfonate is intended to denote a di- or higher sulfonate. Disulfonates and higher sulfonates may be formed as byproducts during the sulfonation of internal olefins followed by the alkaline hydrolysis. A low polysulfonate content in the IOS may improve the physical stability of compositions prepared therefrom (no phase separation). In the IOS, the polysulfonate content, based on the total weight of the IOS, is preferably of at most 2 wt. %, more preferably of at most 1 wt. %. For practical reasons, the lower limit for polysulfonates in the IOS is generally no less than 0.0005 wt. %, based on the weight of the IOS.

Both hydroxy alkane sulfonates and alkene sulfonates are generally formed during the sulfonation of internal olefins followed by the alkaline hydrolysis. Thus, the IOS is usually a mixture comprising at least one hydroxy alkane sulfonate and at least one alkene sulfonate.

As herein used:
  the terms "hydroxy alkane sulfonate" are intended to denote an alkane that is substituted by at least one hydroxyl group and least one sulfonate (—$SO_3^-$ group);
  the term "alkene" encompasses compounds comprising one and only one carbon-carbon double bond (mono-olefins) as well as compounds comprising several carbon-carbon double bond (diolefins and higher olefins);
  the terms "alkene sulfonate" are intended to denote an alkene, as above defined, that is substituted by at least one sulfonate (—$SO_3^-$) group.

In general, the at least one hydroxy alkane sulfonate is composed of at least one hydroxy alkane monosulfonate, or of at least one hydroxy alkane monosulfonate and at least one hydroxy alkane polysulfonate. Hydroxy alkane di- and higher sulfonates may be formed as byproducts during the sulfonation of internal olefins followed by the alkaline hydrolysis.

Likewise, the at least one alkene sulfonate is composed of at least one alkene monosulfonate, or of at least one alkene monosulfonate and at least one alkene polysulfonate. Alkene di- and higher sulfonates may be formed as byproducts during the sulfonation of internal olefins followed by the alkaline hydrolysis.

The at least one hydroxy alkane sulfonate comprised in the IOS may be composed of at least one monohydroxy alkane sulfonate or of at least one monohydroxy alkane sulfonate and at least one polyhydroxy alkane polysulfonate. Preferably, the hydroxy alkane sulfonate is free of or is essentially free of polyhydroxy alkane polysulfonates, which ones may be formed by the sulfonation of di- or higher olefins comprised in the internal olefin manufactured by the process $P^2$.

The at least one alkene sulfonate comprised in the IOS may be composed of at least one mono-olefin sulfonate or of at least one mono-olefin sulfonate and at least one polyolefin sulfonate (which often includes at least one polyolefin polysulfonate). Preferably, the alkene sulfonate is free of, is essentially free of or comprises a low amount of polyolefin polysulfonates, including diolefin disulfonates and/or higher olefin polysulfonates. More generally, it is preferred that the alkene sulfonate be free of, be essentially free of or comprises a low amount of polyolefin sulfonates, including diolefin or higher olefin monosulfonates and polyolefin polysulfonates. Polyolefin sulfonates may be formed as byproducts during the sulfonation of internal mono-olefins or by the mono- or polysulfonation of polyolefins (di- or higher olefins) comprised in the internal olefin manufactured by the process $P^2$.

Still other sulfonates may be formed during the sulfonation of internal olefins. For example, hydroxy mono-olefin sulfonates may be formed, concurrently with diolefin sulfonates, by the monosulfonation of diolefins comprised in the internal olefin manufactured by the process $P^2$. Hydroxy diolefin sulfonates may also be formed as by-products.

A low content of di- or higher olefin sulfonate in the IOS may improve the physical stability of the compositions prepared therefrom (no phase separation). Therefore, in the IOS, the polyolefin sulfonate content, based on the total weight of the IOS, is preferably of at most 2 wt. %, more preferably at most 1 wt. %. For practical reasons, the lower limit for polyolefin sulfonate in the IOS is generally no less than 0.0005 wt. %, based on the weight of the IOS.

To reduce the formation of polysulfonates, of polyhydroxy polysulfonates and of polyolefin sulfonates (especially of polyolefin polysulfonates), the fatty acid, fatty acid derivative or mixture thereof which is used as starting material of the process $P^0$ is desirably an alkane carboxylic acid, an alkane carboxylic acid derivative or a mixture thereof.

In the IOS, the combined weight amount of hydroxy alkane monosulfonate and mono-olefin monosulfonate, based on the total weight of the IOS, is generally of at least 90%, preferably of at least 95%, more preferably at least 98%, still more preferably at least 99%.

In the IOS, the weight ratio of hydroxy alkane monosulfonate to mono-olefin sulfonate is quite often greater than 1 and no more than 20. The weight ratio of hydroxy alkane monosulfonate to mono-olefin sulfonate is preferably of at least 3.25 and more preferably of at least 4.5. An IOS wherein the weight ratio of hydroxy sulfonate to alkene sulfonate is at of least 3.25 has significantly reduced tendency to physically separate and in most cases forms compositions that are fully physically stable.

Sulfonation of the Internal Olefins

In accordance with the process $P^3$, the internal olefin manufactured by the process $P^2$ is further sulfonated to form a sultone.

To this purpose, the internal olefin is typically reacted with a sulfonating agent such as sulfur trioxide, sulfuric acid or oleum. Anhydrous $SO_3$ is preferred.

The sultone that is formed is composed of at least one beta-sultone or of at least one beta-sultone and at least one sultone other than a beta-sultone, like a gamma-sultone, a delta-sultone, an epsilon-sultone or a mixture thereof. In general, more than 50 wt. % of the sultone is beta-sultone.

Together with the sultone, an amount of alkene sulfonic acid may be formed as side product.

According to a first embodiment, the sulfonation is carried out in a falling film reactor.

The falling film reactor is advantageously equipped with cooling means in order to prevent or limit temperature increase in the reactor due to the high exothermicity of the reaction. Desirably, the temperature in the reactor does not exceed 80° C.; more desirably, it is of at most 50° C. Then, for example, the reactor may be equipped with a cooling jacket supplied with cold water; the temperature of the cooling jacket is usually set-up at around 0° to 30° C., possibly at around 0° to 10° C.

A gas flow consisting of a mixture of the sulfonating agent (e.g. anhydrous $SO_3$) diluted with an inert gas at a concentration usually in the range of from 0.5 to 10% v/v, preferably of from 1 to 5% v/v (particularly preferred around 2.5% v/v) is preferably contacted with a falling film of the liquid olefin. The inert gas may be nitrogen or air, and it has been advantageously carefully dried before forming the mixture with the sulfonating agent.

The flows of gas and liquid phases are set-up in order to ensure:
 a residence time generally of from 10 seconds to 10 min, preferably of from 1 min to 6 min (e.g. 3 minutes)
 and
 a mole ratio $SO_3$:internal olefin generally in the range of from 0.7:1 to 1.5:1, preferably of from 0.8:1 to 1.2:1, more preferably of from 0.9:1 to 1.1:1 and still more preferably of about 1.05:1
 in the falling film reactor.

When using a mixture of internal olefins with different chain lengths (and thus different molecular weights) the total molar flow of internal olefins can be calculated using the average molecular weight of the mixture of olefins.

According to a 2nd embodiment, a sulfonating reagent which is a complex of a sulfonating agent with an organic solvent is formed in situ in a reactor.

The sulfonation is generally carried out batchwise in the reactor. The reactor is advantageously equipped with a mechanical stirring in the liquid phase.

A complexing organic solvent (possibly, an ether such as dioxane) may be mixed with a non-complexing organic solvent (possibly, a halogenated solvent such as anhydrous trichloromethane) to form an organic solvent mixture.

Alternatively, the complexing organic solvent may be used alone, without being admixed with any non-complexing organic solvent.

The organic solvent mixture or the complexing organic solvent taken alone, as the case may be, is cooled down to a temperature typically in the range of from −10° C. to 25° C., preferably from −5° C. to 10° C.

Then, a liquid sulfonating agent (for example, liquid $SO_3$) is added to the organic solvent mixture or to the complexing organic solvent to generate the sulfonating agent-complexing organic solvent complex.

Advantageously, this complex precipitates out from the organic solvent mixture. The addition of the liquid sulfonating agent is desirably made slowly and under stirring. When $SO_3$ is the sulfonating agent and dioxane is the complexing agent, about 2 molar equivalents of $SO_3$ can be used to generate the 503-dioxane complex.

The internal olefin is then reacted with the complex sulfonating agent-complexing organic solvent. The reaction is advantageously made under stirring and at a temperature T° of from −10° C. to 15° C., preferably from −5° C. to 10° C. The molar ratio internal olefin:sulfonating agent may range from 0.5 to 2 and can be of about 1.

The reaction medium comprising the internal olefin and the complex sulfonating agent-complexing organic solvent is maintained at temperature T° for a time sufficient for allowing the formation of the sultone. This time may range from 0.3 h to 3 h. The reaction medium may then be allowed to warm up to room temperature (e.g. to a temperature between 15° C. and 30° C.).

All the volatiles (possibly, the complexing organic solvent—e.g. dioxane—or the non-complexing organic solvent—e.g. $CHCl_3$—and the complexing organic solvent—e.g. dioxane —) are then advantageously removed under vacuum.

Optional Aging

Following the sulfonation reaction, the mixture exiting the reactor (composed mainly of beta-sultones) can be allowed to age in order to allow isomerization & trans-sulfonation to occur and to increase the conversion of starting olefins.

During aging, some beta-sultones may be converted into gamma-sultones which may in turn be converted into delta-sultones. Also some beta-sultones may be converted to alkene sulfonic acids.

Alkaline Hydrolysis of the Sultones

In accordance with the process $P^3$, the sultone is subjected to an alkaline hydrolysis, so as to form the internal olefin sulfonate.

To this end, the sultone may be fed to a neutralization/hydrolysis unit comprising a reactor. The reactor is preferably equipped with a mechanical stirring.

The neutralization/hydrolysis can be carried out with a water soluble base, such as a hydroxide, a carbonate, a bicarbonate and/or an amine compound. Among the water soluble bases, sodium hydroxide and sodium carbonate can be cited. The corresponding bases derived from potassium or ammonium are also suitable.

The neutralization is generally carried out with excessive base, calculated on the acid component.

Generally, neutralization is carried out at a temperature in the range of from 0° C. to 40° C.

Hydrolysis may be carried out at a temperature above 50° C. up to 250° C., preferably from 80° C. to 200° C.

The hydrolysis time generally may be from 5 minutes to 4 hours.

During this stage of the process, the sultones are transformed into the desired Internal Olefin Sulfonates through a ring opening reaction.

The sulfonation, digestion and hydrolysis reactions can be followed using NMR analysis. At the end of the process the amount of water in the medium may be adjusted in order to reach an aqueous solution of IOS with a desired concentration of active matter.

Uses of the Products Manufactured by Processes $P^1$, $P^2$ and $P^3$

The internal olefin sulfonate (IOS) manufactured by the process $P^3$ can be notably used in enhanced oil recovery (EOR) application, in particular as oil displacement agent in alkaline-surfactant-polymer (ASP) flooding system.

In addition of its possible use as reaction intermediate in the manufacture of the IOS manufactured by the process $P^3$, the internal olefin manufactured by the process $P^2$ can be notably used as component of a synthetic drilling fluid. It can also be used as lubricant. It can also be used in a paper sizing application.

In addition to its possible use as reaction intermediate in the manufacture of the internal olefin manufactured by the process $P^2$, the secondary fatty alcohol manufactured by the process $P^1$ can be notably used as solvent, as preservative, etc. It can also serve as intermediate for the preparation of a compounds other than an IOS, for example a non-ionic surfactant (by alkoxylating the secondary fatty alcohol).

Advantages of the Present Invention

The processes $P^1$, $P^2$ and $P^3$ of the present invention offer an easy access to secondary fatty alcohols, internal olefins and olefin internal sulfonates. These products are prepared from internal ketone intermediates by a process P0 which yields the desired internal ketones in high yield with only minor amounts (if at all) of undesired by-products being obtained and which can be easily separated from the reaction mixture.

The following examples show the effectiveness of the invented processes and further explain the processes of the present invention. Should the disclosure of any patents, patent applications, and publications which are incorporated herein by reference conflict with the description of the present application to the extent that it may render a term unclear, the present description shall take precedence.

The following examples further explain the present invention.

EXAMPLES

Example 1—Synthesis of a $C_{15}$-$C_{35}$ Ketones Cut Starting from a $C_8$-$C_{18}$ Coco Saturated Fatty Acids Cut (in Accordance with the Process Described in WO 2016177842)

The reaction is carried under argon in a 750 ml reactor equipped with mechanical stirring, Dean-Stark apparatus and an addition funnel. In the reactor, 6.8 g (0.12 mol) of iron powder is dispensed and 200 g (0.97 mol) of the coco saturated fatty acids cut (with the following distribution: $C_8$: 7 wt %, $C_{10}$: 8 wt %, $C_{12}$: 48 wt %, $C_{14}$: 17 wt %, $C_{16}$: 10 wt %, $C_{18}$: 10 wt %) are introduced into the addition funnel.

A first partial amount of 50 g of fatty acids is added into the reactor and the temperature is brought to 250° C. The mixture is stirred at this temperature during 4 h. During this time the color of the media changes to black and $H_2$ gas is released. FTIR analysis of the crude mixture shows complete formation of intermediate iron carboxylate complexes.

The temperature is then raised to 330° C. and the mixture is stirred at this temperature during 2 h. During this period of time, the intermediate iron carboxylate complexes are decomposed to fatty ketones, iron oxide and $CO_2$.

The remaining fatty acids (150 g) are slowly introduced into the reactor, at a flow rate such that the temperature of the reaction medium does not fall down below 320° C. and which allows keeping the concentration of fatty acids in the reaction medium very low. An average addition flow rate of around 25 g fatty acids/hour proves to be satisfactory. Practically, this is achieved through the successive slow additions (1 hour per addition) of 3 portions of 50 g of melted fatty acids followed by 1 hour of stirring at 330° C. between each addition.

At the end of the third and last addition, the crude medium is stirred at 330° C. during 2 h and the reaction progress is monitored through FTIR. When the reaction is completed (no more iron complex detected by FTIR), the mixture is allowed to cool down at room temperature and 400 ml of $CHCl_3$ is added to the crude media. The mixture is stirred at 40° C. in order to solubilize the product ($C_{15}$-$C_{35}$ ketones). The obtained suspension is filtered on a silica plug (400 g) and eluted using 3 liters of chloroform. Evaporation of the solvent affords 161 g (0.46 mol) of the product O15-O35 ketones as an analytically pure white wax (95% isolated yield).

Example 2—Ketonization of $C_8$-$C_{18}$ Fatty Acids Cut Using Magnetite $Fe_3O_4$ as the Catalyst (in Accordance with Process $P^0$)

The reaction is carried out under an inert atmosphere of argon.

In a 750 ml reactor equipped with a mechanical stirrer, a Dean-Stark apparatus to trap water generated during the reaction and an addition funnel, are dispensed 40 g of the $C_{15}$-$C_{35}$ ketones made by example 1 and 9.3 g (0.040 mole) of magnetite $Fe_3O_4$.

The addition funnel of the reactor is filled with 200 g (0.970 mole) of melted fatty acids ($C_8$: 7 wt %, $C_{10}$: 8 wt %, $C_{12}$: 48 wt %, $C_{14}$: 17 wt %, $C_{16}$: 10 wt %, $C_{18}$: 10 wt %).

The reaction mixture is then heated at 330° C. under stirring (500 rpm) and 200 g (0.970 mole) of the melted fatty acids is slowly introduced into the reactor such that the temperature of the reaction medium does not fall down below 320° C. (for example with an addition flow rate of around 25 g fatty acids/hour).

Practically this can be done also through the successive slow additions (1 hour per addition) of 4 portions of 50 g (60 ml) of melted fatty acids followed by 1 hour of stirring at 330° C. after each addition.

At the end of the last addition, the crude medium is stirred at 330° C. during an additional hour and the reaction progress is monitored through FTIR.

At the end of the reaction when the intermediate iron complex is not detected anymore through FTIR (absorption bands at 1550 cm$^{-1}$ and 1408 cm$^{-1}$), the mixture is allowed to cool down at room temperature and dissolved in 400 ml of $CHCl_3$.

The obtained solution is filtered through a path of 400 g of silica gel followed by elution with 5 liters of $CHCl_3$ in order to remove iron oxide.

The chloroform is evaporated under vacuum and the crude product is dried overnight under 10 mbar at 50° C. to obtain about 207 g of ketone (which contains about 167 g of product generated through ketonization of the 200 g of fatty acids in addition to the 40 g of fatty ketones that have been dispensed initially in the reactor) as a light brown wax corresponding to a crude yield of about 98%.

Analysis of the crude shows a GC purity of about 96% (impurities being mainly hydrocarbons) with the following composition for the ketones cut:

$C_{15}$: about 0.5 wt %, $C_{17}$: about 1.3 wt %, $C_{19}$: about 8.4 wt %, 021 about 11.4 wt %, $C_{23}$: about 28.4 wt %, $C_{25}$: about 19.0 wt %, $C_{27}$: about 13.0 wt %, $C_{29}$: about 11.7 wt %, $C_{31}$: about 3.7 wt %, $C_{33}$: about 1.6 wt %, $C_{35}$: about 0.9 wt %.

Example 3—Ketonization of $C_8$-$C_{18}$ Fatty Acids Cut Using Magnetite $Fe_3O_4$ as the Catalyst (in Accordance with Process $P^0$)

The reaction is carried out exactly as in example 2 except that the 40 g of $C_{15}$-$C_{35}$ ketones dispensed in the reactor are not the $C_{15}$-$C_{35}$ ketones made by example 1, but the $C_{15}$-$C_{35}$ ketones made by example 2.

As in example 2, about 207 g of ketone are obtained as a light brown wax corresponding to a crude yield of about 98%.

Analysis of the crude shows likewise a GC purity of about 96% (impurities being mainly hydrocarbons) with the following composition for the ketones cut: about 0.5 wt %, $C_{17}$: about 1.3 wt %, $C_{19}$: about 8.4 wt %, $C_{21}$: about 11.4 wt %, $C_{23}$: about 28.4 wt %, $C_{25}$: about 19.0 wt %, $C_{27}$: about 13.0 wt %, $C_{29}$: about 11.7 wt %, $C_{31}$: about 3.7 wt %, $C_{33}$: about 1.6 wt %, $C_{35}$: about 0.9 wt %.

Example 4—Ketonization of $C_8$-$C_{18}$ Fatty Acids Cut Using Fe(III) Oxide $Fe_2O_3$ as the Catalyst (in Accordance with Process $P^0$)

The reaction is carried out under an inert atmosphere of argon.

In a 750 ml reactor equipped with a mechanical stirrer, a Dean-Stark apparatus to trap water generated during the reaction and an addition funnel, are dispensed 40 g of $C_{15}$-$C_{35}$ ketones made by example 2 and 9.74 g (0.060 mole) of $Fe_2O_3$.

The addition funnel is filled with 200 g (0.970 mole) of melted fatty acids ($C_6$: 7 wt %, $C_{10}$: 8 wt %, $C_{12}$: 48 wt %, $C_{14}$: 17 wt %, $C_{16}$: 10 wt %, $C_{18}$: 10 wt %).

The reaction mixture is then heated at 330° C. under stirring (500 rpm) and 200 g (0.970 mole) of the melted fatty acids is slowly introduced into the reactor such that the temperature of the reaction medium does not fall down below 320° C. (for example with an addition flow rate of around 25 g fatty acids/hour).

Practically this can be done through the successive slow additions (1 hour per addition) of 4 portions of 50 g (60 ml) of melted fatty acids with 1 hour of stirring at 330° C. between each addition.

At the end of the last addition, the crude medium is stirred at 330° C. during 0.5 hour and the reaction progress is monitored through FTIR.

At the end of the reaction when the intermediate iron complex is not detected anymore through FTIR (absorption bands at 1550 cm$^{-1}$ and 1408 cm$^{-1}$), the mixture is allowed to cool down at room temperature and dissolved in 300 ml of $CHCl_3$.

The obtained solution is filtered through a path of 400 g of silica gel followed by elution with 3 liters of $CHCl_3$ in order to remove iron oxide.

The chloroform is evaporated under vacuum and the crude product dried overnight under 10 mbar at 50° C. to obtain about 204 g of ketone (about 164 g of product generated through ketonization of the 200 g of fatty acids in addition to the 40 g of fatty ketones that have been dispensed initially in the reactor) as a light brown wax corresponding to a crude yield of about 96%.

Analysis of the crude shows a GC purity of about 97% (impurities being mainly alkanes) with the following composition for the ketones cut:

$C_{15}$: about 0.5 wt %, $C_{17}$: about 1.2 wt %, $C_{19}$: about 8.4 wt %, $C_{21}$: about 11.2 wt %, $C_{23}$: about 28.6 wt %, $C_{25}$: about 19.1 wt %, $C_{27}$: about 13.2 wt %, $C_{29}$: about 11.4 wt %, $C_{31}$: about 3.5 wt %, $C_{33}$: about 1.5 wt %, $C_{35}$: about 0.7 wt %.

Example 5 (Comparative)—Ketonization of $C_8$-$C_{18}$ Fatty Acids Cut Using Magnetite $Fe_3O_4$ as the Catalyst with Direct Introduction of Entire Amount of Fatty Acids to be Converted and without Initial Introduction of Ketone The reaction is carried out under an inert atmosphere of argon.

In a 500 ml round bottom flask equipped with a mechanical stirrer and a Dean-Stark apparatus to trap water generated during the reaction, 100 g (0.480 mole) of melted fatty acids ($C_8$: 7 wt %, $C_{10}$: 8 wt %, $C_{12}$: 48 wt %, $C_{14}$: 17 wt %, $C_{18}$: 10 wt %, $C_{18}$: 10 wt %) and 4.7 g (0.020 mole) of magnetite $Fe_3O_4$ are dispensed.

The mixture is then allowed to stir under reflux (330° C. ordered) during 8 hours. The reaction media temperature increases progressively over the course of the reaction from 250° C. (beginning) to 303° C. after 8 hours of stirring. Importantly generation of water is observed and at the end of the reaction GC analysis (normalization) shows approximately that the conversion of fatty acids is around 40%

(significant amounts of fatty acids remaining), the selectivity of ketone formation is about 55% and the approximate yield of ketones is only 23%.

Example 6—Conversion of Internal Ketones to Secondary Fatty Alcohols (in Accordance with Process $P^0$)

This example describes the hydrogenation of the internal ketones obtained in accordance with the process $P^0$ to obtain the corresponding secondary fatty acid alcohols.

The hydrogenation is carried out on a $C_{15}$-$C_{35}$ cut of internal fatty ketones obtained by example 3 in a 750 ml autoclave equipped with a Rushton turbine, without any added solvent.

28 g of Pd/C (3%) and 280 g of the $C_{15}$-$C_{35}$ fatty ketones made by example 3 are introduced into the reactor which is sealed. Then the temperature is brought to 80° C. and the mixture is stirred at 1000 rpm.

The reactor atmosphere is purged 3 times with 4 MPa of nitrogen then 3 times with 3 MPa of hydrogen.

The temperature is then raised to 150° C. and the mixture is stirred at this temperature maintaining 3 MPa of hydrogen until completion of the reaction (monitored by GC analysis).

At the end of the reaction, the mixture is allowed to cool down to 80° C. and the reactor is purged with nitrogen.

A $1^{st}$ crop of secondary fatty alcohol product (about 180 g) is obtained through filtration and the remaining part is extracted using 400 ml of hot toluene. After evaporation of the solvent, a total amount of about 247 g of secondary fatty alcohol white solid is obtained corresponding to an isolated yield of about 88%.

The secondary fatty alcohol product is cut of $C_{15}$-$C_{35}$ secondary alcohols.

Example 7—Dehydration of Secondary Fatty Alcohols to Internal Olefins (in Accordance with Process $P^2$)

In this example, the secondary fatty alcohols obtained in example 6 (according to process $P^1$) are dehydrated with limited isomerization of C=C bond.

The dehydration reaction is carried out under argon atmosphere, without added solvent and using $Al_2O_3$-η as a catalyst.

47 g of a cut of internal alcohols obtained in accordance with example 6 followed by 4.7 g of $Al_2O_3$-η are added in a round bottom flask equipped with a Dean-Stark apparatus and magnetic stirring. The mixture is then stirred at 300° C. during 2 hours. Water generated during the dehydration reaction is trapped with the Dean-Stark apparatus.

After completion of the dehydration reaction, the product is extracted using 150 ml of hot toluene. After evaporation of the solvent, the product is obtained as pale yellow liquid (about 39 g) corresponding to an isolated yield of about 87%.

The pale yellow liquid product consists essentially of a cut of $C_{15}$-$C_{35}$ internal olefins with C=C bond localized almost in the middle of the chain.

Example 8—Conversion of Internal Olefins into Internal Olefin Sulfonates (in Accordance with Process $P^3$)

In this example, the liquid internal olefins obtained in example 7 (according to process $P^2$) are converted into internal olefin sulfonates (IOS).

Firstly, the internal olefins undergo a sulfonation reaction in a falling film (lab scale film) reactor equipped with a cooling jacket supplied with cold water in order to prevent temperature increases in the reactor due to the high exothermicity of the reaction. For this reaction, the temperature of the cooling jacket is set-up at around 4° C.

A gas flow consisting of a mixture of anhydrous $SO_3$ diluted with carefully dried nitrogen, with a $SO_3$ concentration usually of 2.5% v/v, is contacted with the falling film of liquid olefins. The flows of gas and liquid phases are set-up in order to ensure a residence time of 3 minutes in the reactor and a mole ratio $SO_3$:internal olefin of 1.05:1.

Following the sulfonation reaction the mixture exiting the reactor (which is composed mainly of 6-sultones) is allowed to age for 1 day in order to allow isomerization & trans-sulfonation to occur and to increase the conversion of starting olefins.

Thereafter, the obtained mixture is neutralized using an aqueous solution of NaOH (10 wt. %) in a reactor equipped with a mechanical stirring. Hydrolysis is then carried out by heating the mixture under mechanical stirring. During this stage of the process, the sultones are transformed into the desired IOS through a ring opening reaction.

The sulfonation, digestion and hydrolysis reactions are followed using NMR analysis.

Example 9—Conversion of Internal Olefins into Internal Olefin Sulfonates (in Accordance with Process $P^3$)

In this other example, the sulfonation of the liquid internal olefins obtained in example 7 (according to process $P^2$) is carried out in a batch reactor equipped with a mechanical stirring in the liquid phase using an in-situ prepared sulfonating reagent, namely $SO_3$-dioxane complex.

In a round bottom flask anhydrous dioxane and anhydrous trichloromethane (mixture ratio 1:35 v/v) are mixed and cooled down to a temperature of 0° C. Then liquid $SO_3$ (2 molar equivalents) is slowly added under stirring during 10 minutes to generate the complex $SO_3$-dioxane which precipitates out from the mixture as white crystals.

The internal olefins made according to example 7 (1 equivalent) are then slowly added under stirring at a temperature of 0° C. to the reaction medium during a period of 1 hour and the mixture is allowed to warm up to room temperature. During this time, the color of the mixture changes from light yellow to dark brown and NMR analysis indicates that almost full completion of internal olefins has occurred (around 94% of olefin conversion to sultones). All the volatiles ($CHCl_3$ and dioxane) are then removed under vacuum.

Then 2.4 equivalents of an aqueous NaOH solution (10 wt. %) are added to the residue and the resulting mixture is stirred at room temperature during 1 hour in order to ensure complete neutralization.

Hydrolysis is then performed by stirring the resulting reaction mixture at 95° C. overnight. NMR analysis indicates full conversion of sultones to internal olefin sulfonates.

At the end of the process the amount of water is adjusted in order to reach an aqueous solution of IOS with a concentration of active matter of 30 wt. %.

Example 10—Conversion of Internal Olefins into Internal Olefin Sulfonates (in Accordance with Process $P^3$)

In accordance with this last example, IOS is prepared by the method of Changxin et al. (Arab. J. Sci. Eng., 2014, vol. 39, pages 37-41).

Sulfonation is carried out in a falling film glass reactor. Gaseous sulfur trioxide is diluted with air, and then passed through the internal fatty olefin obtained by example 7. The ratio of sulfur trioxide to through the internal fatty olefin is 1:1. The concentration of sulfur trioxide in the air is 2.5% by volume. The cooling water inlet temperature is from about 18° C. to about 24° C., and the outlet temperature is from about 23° C. to about 29° C.

No aging of the reaction mixture issued from the sulfonation reactor, hereinafter "the sulfonation product", is applied.

The sulfonation product is neutralized with sodium hydroxide solution, and then hydrolysed for 30 min at 70° C.

Petroleum ether having a boiling point in the range 60~90° C. (analytical reagent) is used to extract most of the unreacted internal olefin.

The product is dried, and was next washed with ethanol. The final product is obtained after evaporation of the ethanol.

The invention claimed is:

1. A process $P^1$ for the manufacture of a secondary fatty alcohol, said process $P^1$ comprising:
   synthesizing an internal ketone $K^1$ by a process $P^0$ comprising the decarboxylative ketonization reaction of a fatty acid, a fatty acid derivative, or a mixture thereof in a liquid phase with a decarboxylative ketonization catalyst comprising a metal compound in a reaction medium, wherein a ketone $K^2$ at liquid state, which is identical or similar to the internal ketone $K^1$, is introduced into the reaction medium, and
   subjecting the internal ketone $K^1$ to a hydrogenation reaction with hydrogen gas as hydrogenating agent to form the secondary fatty alcohol,
   wherein the fatty acid and the fatty acid derivative independently comprise one or more compounds derived from a fatty acid cut, wherein the one or more compounds comprise a hydrocarbon chain having from 4 to 28 carbon atoms attached to a terminal carboxyl group.

2. The process $P^1$ according to claim 1, wherein the ketone $K^2$ has a boiling point of at least 270° C.

3. The process $P^1$ according to claim 1, wherein the difference between the boiling point of the ketone $K^1$ and the boiling point of the ketone $K^2$ is equal to or lower than 40° C.

4. The process $P^1$ according to claim 1, wherein a fatty acid is used as starting material and the fatty acid is a mixture of carboxylic acid selected from the group consisting of caprylic acid, capric acid, lauric acid, myristic acid, palmitic acid, stearic acid and mixtures thereof.

5. The process $P^1$ according to claim 1, wherein the reaction medium is substantially free of third solvents.

6. The process $P^1$ according to claim 1, wherein the ketone $K^2$ is identical to ketone $K^1$ and has been synthesized in accordance with a previous process $P^0$.

7. The process $P^1$ according to claim 1, wherein the process $P^0$ comprises the steps of:
   a) introducing in any order at least part of the ketone $K^2$ at liquid state, at least part of the metal compounds, at least part of the fatty acid, fatty acid derivative or mixture thereof into a reactor in order to synthesize the ketone $K^1$, said reactor optionally containing before said introduction, a part of the metal compounds, and/or a part of the fatty acid, fatty acid derivative or mixture thereof and/or a part of the ketone $K^2$ and/or a part of the ketone $K^1$,
   b) recovering the ketone $K^1$ optionally together with the ketone $K^2$,
   c) optionally recycling at least part of the ketone $K^1$ and/or ketone $K^2$ and/or at least part of the metal compounds to step a).

8. The process $P^1$ according to claim 7, wherein step a) of process $P^0$ comprises the steps of:
   a1) introducing at least part of the ketone $K^2$ at liquid state, and at least part of the metal compounds into a reactor, said reactor being free of fatty acid(s) and fatty acid derivatives(s),
   a2) introducing the fatty acid, fatty acid derivative or mixture thereof into the reactor, optionally with:
      a part of the metal compounds, and/or
      a part of the ketone $K^2$.

9. The process $P^1$ according to claim 7, wherein at step a) of process $P^0$, the fatty acid, fatty acid derivative or mixture thereof is introduced sequentially or continuously into the reactor.

10. A process $P^2$ for the manufacture of an internal olefin, said process $P^2$ comprising:
    manufacturing a secondary fatty alcohol by the process $P^1$ according to claim 1, and
    converting the secondary fatty alcohol into an internal olefin by a dehydration reaction.

11. A process $P^3$ for the manufacture of an internal olefin sulfonate, said process $P^3$ comprising:
    manufacturing an internal olefin by the process $P^2$ according to claim 10,
    sulfonating the internal olefin to form a sultone, and
    subjecting the sultone to an alkaline hydrolysis, so as to form the internal olefin sulfonate.

12. The process $P^1$ according to claim 2, wherein the ketone $K^2$ has a boiling point of at least 290° C.

13. The process $P^1$ according to claim 3, wherein the difference between the boiling point of the ketone $K^1$ and the boiling point of the ketone $K^2$ is equal to or lower than 10° C.

14. The process P1 according to claim 1, wherein the metal compound is selected from the group consisting of magnesium, iron and their oxides.

15. The process P1 according to claim 14, wherein the metal compound is iron powder.

16. The process $P^1$ according to claim 14, wherein the metal compound is FeO, $Fe_3O_4$, or $Fe_2O_3$.

17. The process $P^1$ according to claim 16, wherein the total amount of fatty acid and fatty acid derivative added in the reaction medium for the decarboxylative ketonization reaction is such that the overall molar ratio of metal to carboxylic groups is in the range of from 1:6 to 1:99.

18. The process $P^1$ according to claim 1, wherein the temperature of the reaction medium inside the reactor is maintained from 285° C. to 350° C. during the decarboxylative ketonization reaction.

19. The process $P^1$ according to claim 1, wherein an intermediate metal carboxylate salt which is substantially soluble in the reaction medium is formed through an initial reaction between the fatty acid or its derivative with the metal compound.

20. The process $P^1$ according to claim 1, wherein the process $P^0$ is a batch process.

21. The process $P^1$ according to claim 4, wherein the mixture of fatty acids comprises a fatty acid cut obtained from coconut oil.

* * * * *